US010786212B1

(12) United States Patent
Guo et al.

(10) Patent No.: US 10,786,212 B1
(45) Date of Patent: Sep. 29, 2020

(54) SYSTEM AND METHOD OF HELICAL CARDIAC CONE BEAM RECONSTRUCTION

(71) Applicant: FMI Medical Systems, Inc., Solon, OH (US)

(72) Inventors: Hongbin Guo, Champaign, IL (US); Qing Ye, Solon, OH (US)

(73) Assignee: Minfound Medical Systems Co., Ltd., Hangzhou, Zhejiang (CN)

( * ) Notice: Subject to any disclaimer, the term of this patent is extended or adjusted under 35 U.S.C. 154(b) by 0 days.

(21) Appl. No.: 16/427,953

(22) Filed: May 31, 2019

(51) Int. Cl.
*A61B 6/02* (2006.01)
*A61B 6/00* (2006.01)
*A61B 6/03* (2006.01)

(52) U.S. Cl.
CPC ............ *A61B 6/027* (2013.01); *A61B 6/4085* (2013.01); *A61B 6/4447* (2013.01); *A61B 6/503* (2013.01); *A61B 6/032* (2013.01); *A61B 6/584* (2013.01)

(58) Field of Classification Search
CPC ...... A61B 6/4085; A61B 6/4447; A61B 6/503
See application file for complete search history.

(56) References Cited

U.S. PATENT DOCUMENTS

| 8,184,883 | B2 | 5/2012 | Grass et al. |
| 2006/0198491 | A1 | 9/2006 | Taguchi |
| 2007/0269000 | A1* | 11/2007 | Partain ................. A61B 6/4241 378/37 |
| 2008/0267455 | A1 | 10/2008 | Grass et al. |
| 2018/0055460 | A1* | 3/2018 | Matthews ............ A61B 6/5294 |

FOREIGN PATENT DOCUMENTS

| EP | 2452626 B1 | 9/2013 |
| EP | 2030170 B1 | 1/2019 |

* cited by examiner

*Primary Examiner* — Edward Park
(74) *Attorney, Agent, or Firm* — Fishman Stewart PLLC

(57) ABSTRACT

A computed tomography (CT) system includes a rotatable gantry having an opening to receive an object to be scanned, an x-ray tube, a pixelated detector positioned on the rotatable gantry to receive the x-rays from the x-ray tube, and a computer programmed to acquire helical CT data, determine a sunrise (SR) view position for each pixel within a SR index image, and determine a sunset (SS) view position for each pixel within a SS index image, for a given reference image slice, wherein the SR view position is a first angle of an illumination range for a voxel and the SS view position is a last angle of the illumination range for the voxel, for all slices, rotate the SR index image and the SS index image through a projection index, and reconstruct an image based on the rotated SR index image and the SS index image.

18 Claims, 7 Drawing Sheets

SYSTEM AND METHOD OF HELICAL CARDIAC CONE BEAM RECONSTRUCTION

TECHNICAL FIELD

This disclosure relates generally to diagnostic imaging and, more particularly, to an apparatus and method of helical cardiac cone beam reconstruction in a computed tomography (CT) system.

BACKGROUND

Typically, in computed tomography (CT) imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector. Imaging data may be obtained using x-rays that are generated at a single polychromatic energy. However, some systems may obtain multi-energy images that provide additional information for generating images.

Third generation multi-slices CT scanners typically include a detector assembly having scintillator/photodiodes arrays positioned in an arc, where the focal spot is the center of the corresponding circle. The material used in these detectors generally has scintillation crystal/photodiode arrays, where the scintillation crystal absorbs x-rays and converts the absorbed energy into visible light. A photodiode is used to convert the light to an electric current. The reading is typically proportional and linear to the total energy absorbed in the scintillator.

In X-ray computed tomography (CT) imaging systems that include increased detector width, such as for post-64 row CT scanners, provide sufficient axial coverage such that the whole heart can be imaged in one rotation. However, for CT scanners having 64 rows, or less than 64 rows, retrospective helical scanning is commonly performed. That is, by using an electrocardiogram (ECG) signal, heart beat rate control and reconstruction algorithms can obtain cardiac images having satisfactory quality.

According to one known algorithm, retrospectively gated cardiac reconstruction for helical data can be integrated into a known cone beam reconstruction framework. This known method, sometimes referred to as extended cardiac reconstruction (ECR), is an approximate helical cone beam reconstruction method. A high redundancy of helical projection data is obtained using a low pitch helical acquisition mode. A subset of acquired data is selected to restrict the information integrated in the image volume to a defined motion state of the heart. The obtained data is rebinned from fan geometry to parallel geometry and the rebinned projection is filtered by a one-dimensional ramp filtering kernel. A cosine cone angle weighing is applied and then a 3D weighted backprojection is performed.

Such a small pitch implies a huge data set, thus if each voxel is reconstructed by checking all available projections the computation will be extremely slow and impractical to implement. Thus the illumination range is typically computed for each voxel first to exclude a large number of projections. However, the illumination range computation itself is not an easy task and can take a significant amount of time since the illumination range is different for every voxel.

However, in retrospective helical cardiac reconstruction, the illumination window computation for each voxel is different and the computation can be very computationally intense and time consuming. That is, the illumination range is typically computed for each voxel first to exclude a large number of projections before the reconstruction.

Thus, there is a need to improve the reconstruction time in helical scan reconstruction.

BRIEF DESCRIPTION

The disclosure is directed toward an apparatus, method of fabricating, and method of accelerating the computation of illumination range of each pixel.

A computed tomography (CT) system includes a rotatable gantry having an opening to receive an object to be scanned, an x-ray tube, a pixelated detector positioned on the rotatable gantry to receive the x-rays from the x-ray tube, and a computer programmed to acquire helical CT data, determine a sunrise (SR) view position for each pixel within a SR index image, and determine a sunset (SS) view position for each pixel within a SS index image, for a given reference image slice, wherein the SR view position is a first angle of an illumination range for a voxel and the SS view position is a last angle of the illumination range for the voxel, for all slices, rotate the SR index image and the SS index image through a projection index, and reconstruct an image based on the rotated SR index image and the SS index image.

A method of computed tomography (CT) imaging includes rotating an object on a rotatable CT gantry, generating x-rays toward the object from an x-ray tube, positioning a pixelated detector on the rotatable gantry to receive the x-rays from the x-ray tube, acquiring helical CT data, determining a sunrise (SR) view position for each pixel within a SR index image, and a sunset (SS) view position for each pixel within a SS index image, for a given reference image slice, wherein the SR view position is a first angle of an illumination range for a voxel and the SS view position is a last angle of the illumination range for the voxel, for all slices, mathematically rotating the SR index image and the SS index image through a projection index, and reconstructing an image based on the rotated SR index image and the SS index image.

Various other features and advantages will be made apparent from the following detailed description and the drawings.

DETAILED DESCRIPTION

The operating environment of disclosed examples is described with respect to a multislice computed tomography (CT) system. Examples are described with respect to a "third generation" CT scanner, however it is contemplated that the disclosed examples are applicable to other imaging systems as well, and for CT systems having more or less than the illustrated sixty-four-slice system.

Figure 1:
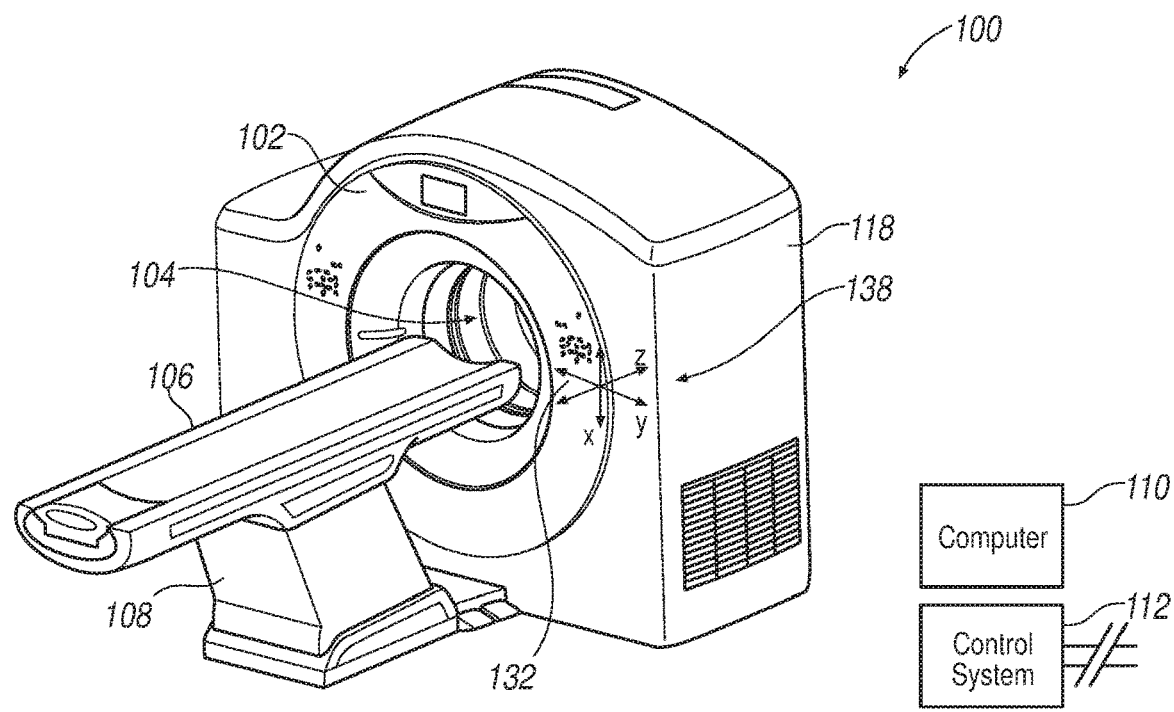
FIG. 1 is a perspective view of a CT imaging system.
Figure 2:
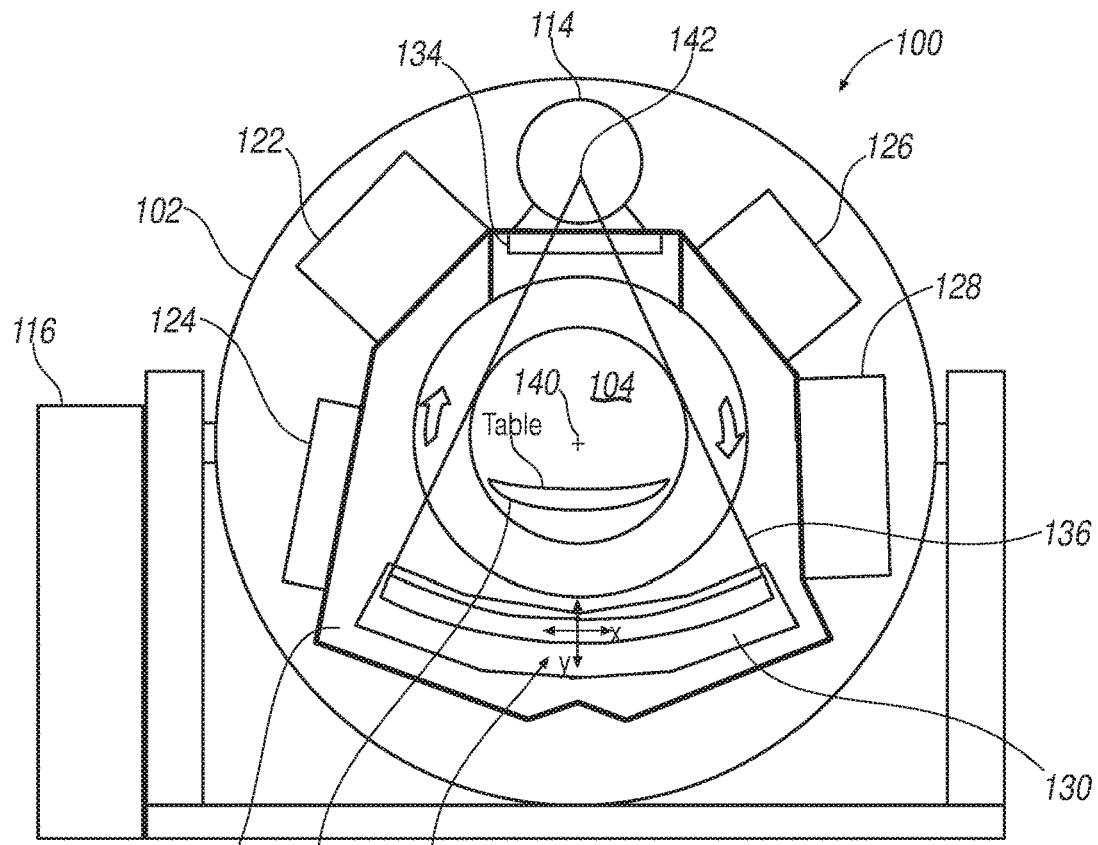
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction programs, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a high-voltage generator 128 for generating high voltage in x-ray tube 114, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is rotated about the patient, and table 106 is enabled to move the patient axially into the opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals that are digitized and passed to DAS 124, and then to computer 110 where the data is further processed to generate an image. The imaging data are stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a center point about which rotatable base rotates, and is an approximate position of the patient for imaging purposes). A focal spot 142 is illustrated within x-ray tube 114, which corresponds to a spot from which x-ray beam 136 emits.

Figure 3:
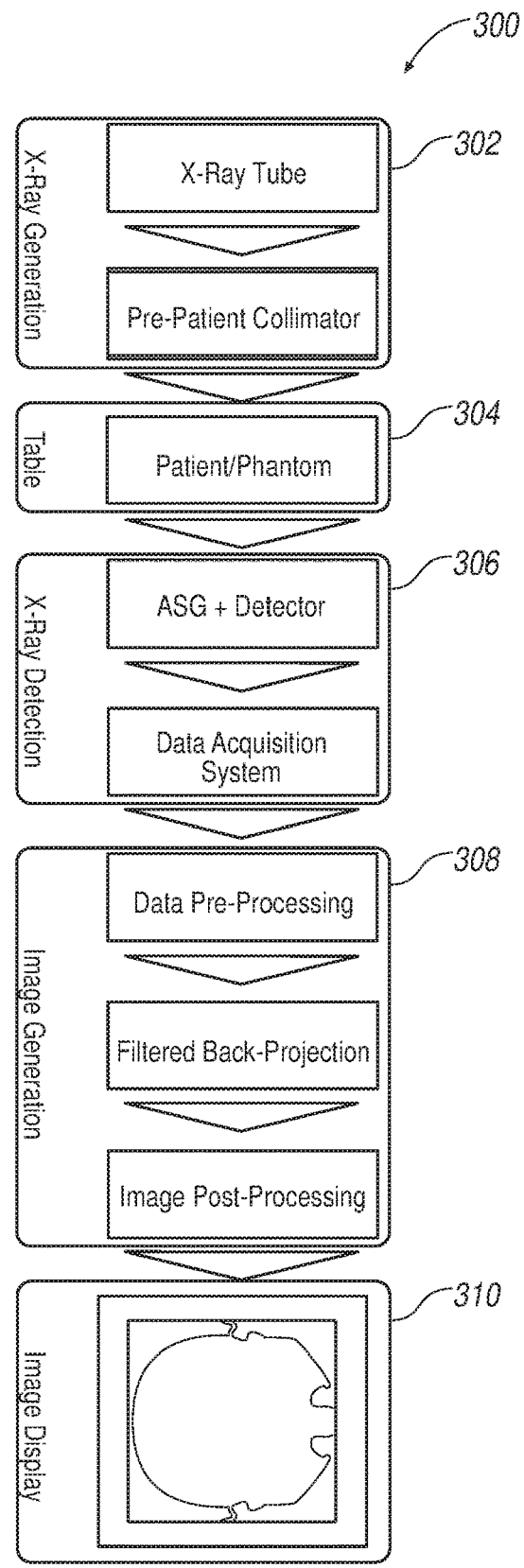
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which patient table 106 passes 304 through opening 104 of gantry 102. In one example table 106 may have a patient thereon, and in another example a phantom may be used for calibration purposes.

X-ray detection 306 occurs when x-rays having been emitted from x-ray tube 114 pass to detector assembly 130. An anti-scatter grid (ASG) prevents x-ray scatter (emitting for example from the patient as secondary x-rays and in a direction that is oblique to x-ray beam 136), by generally filtering x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slip-ring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
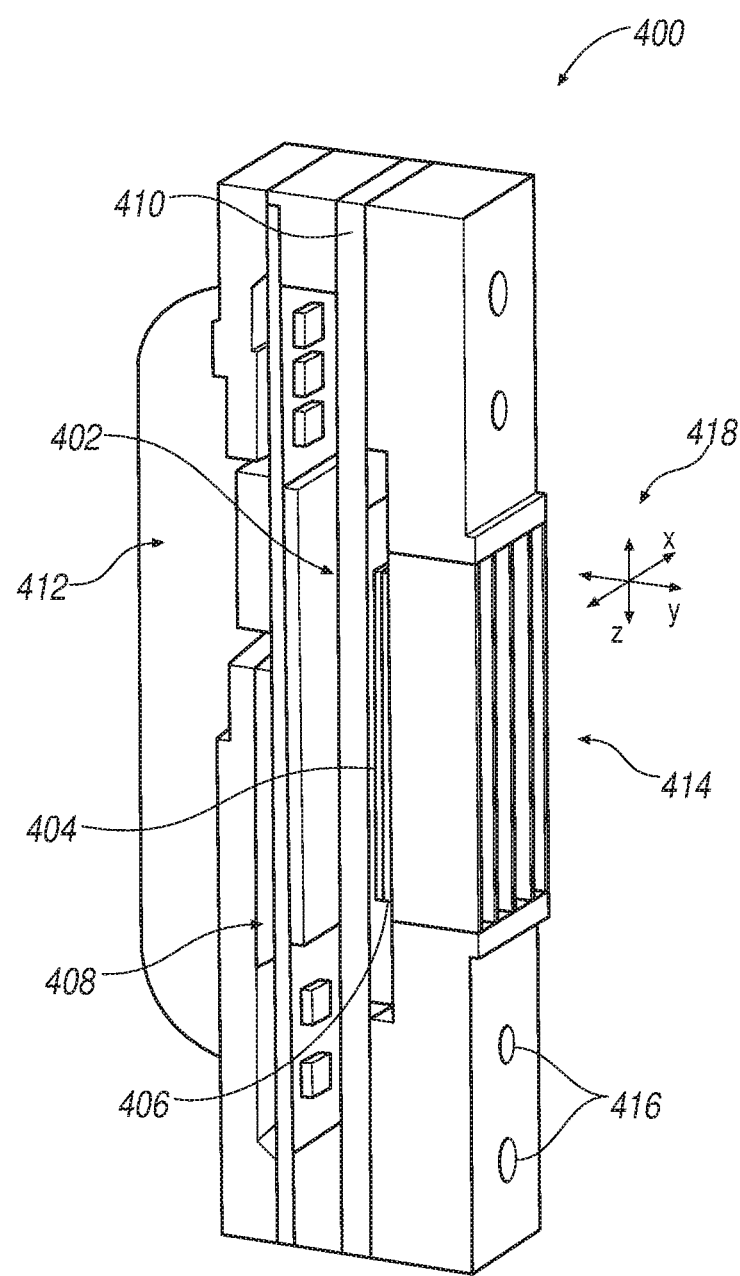
FIG. 4 is an example of a detector module.

FIG. 4 illustrates an exemplary detector module 400 that is one of a plurality of modules for use in detector assembly 130. A diode-scintillator array 402 includes a pixelated scintillator 406 positioned on a pixelated photodiode array 404. The photodiode array 404 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one embodiment, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

As known, retrospectively gated cardiac reconstruction for helical data can be integrated into a known cone beam reconstruction framework. This known method, sometimes referred to as extended cardiac reconstruction (ECR), is an approximate helical cone beam reconstruction method. A high redundancy of helical projection data is obtained using a low pitch helical acquisition mode. A subset of acquired data is selected to restrict the information integrated in the image volume to a defined motion state of the heart. The obtained data is rebinned from fan geometry to parallel geometry and the rebinned projection is filtered by a one-dimensional ramp filtering kernel. A cosine cone angle weighing is applied and then a 3D weighted backprojection is performed, here the weight including ECG gate weight and cone angle weight.

According to the disclosure, multirow X-ray CT cardiac imaging with high time resolution and appropriate space resolution provides a tool for coronary artery imaging, and diagnosis of other types of heart disease. To address heart motion, ECG gating technology is adopted in a cardiac scan and known cone beam cardiac reconstruction algorithms may be employed for reconstruction. For scanners in the market with detector rows less than or equal to 64 retrospective helical cardiac scan is commonly used with small pitch. As such, and according to the disclosure, a helical cardiac reconstruction algorithm is disclosed to give an overall picture of the cardiac reconstruction algorithm, then discussion shifts to the illumination range computation.

Figure 5:
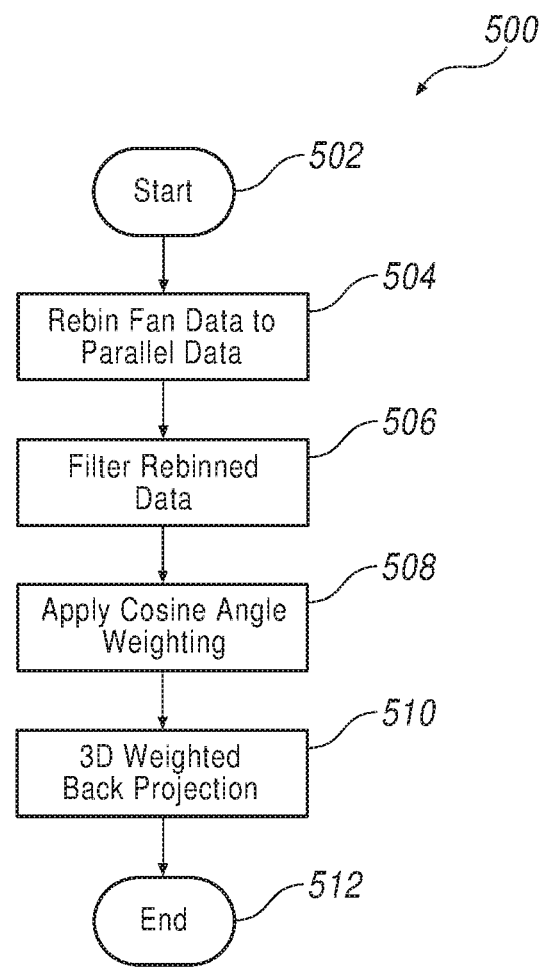
FIG. 5 illustrates steps for a known method having steps for image reconstruction that shows high-level steps for cardiac helical reconstruction.

FIG. 5 illustrates a known method 500 having steps for image reconstruction that shows high-level steps for cardiac helical reconstruction.

Starting at step 502, helical cardiac scanning data of a small pitch h is obtained with multi-row cylindrical detector panel $p_1(y, v, \beta)$. Here y and $\beta$ represent a fan angle of each channel and a source position angle of each projection respectively, variable v stands for the z-coordinate of the detectors at z-axis. At step 504 the fan data is rebinned to parallel data. That is, the projection data $p_1(y, v, \beta)$ is rebinned from fan geometry to parallel geometry for each row v to produce $p_2(u, v, \theta)$. Here (u, v) is a local coordinate for a detector panel passing through the system isocenter, such as isocenter 140 of system 100. Variable u stands for the distance from system isocenter to each channel.

At step 506 the rebinned data is filtered. That is, the rebinned projection is filtered by a one-dimensional ramp filtering kernel K(u), which results in $p_3(u, v, \theta)$. At step 508 cosine angle weighting is applied to yield $p_4(u, v, \theta)$. At step 510 a 3D ECG gate weighted backprojection is performed:

$$f(x) = \frac{1}{2\pi} \int_{\theta_f(x)}^{\theta_l(x)} W_{all}(\theta, x) \cdot p_4(u, v, \theta) d\theta; \qquad \text{Eqn. 1.}$$

Here, $\theta_f(x)$ and $\theta_l(x)$ are the first and last angle of the illumination range for voxel x, which are called sunrise (or otherwise referred to herein as "SR") and sunset (or otherwise referred to herein as "SS"), respectively. The π-partner normalized weight $W_{all}$ is built up from cardiac weight $w_c(\theta)$ and illumination weight $w_i(\theta, x)$. The method ends at step 512.

As such, by employing the retrospective cardiac gating information, the cardiac weight $w_c(\theta)$ selects projection data from a certain motion state duration at which the periodic heart movement remains at a steady state for a short time, the middle point of which is called phase point. To overcome the artifacts introduced through heart movement, a short gating window at the phase point is applied for better time resolution, and the width of the gating window is optimized to balance time resolution with dose efficiency. The 3D backprojection is only performed for the illumination range, or from sunrise to sunset, for each voxel.

Further, for each voxel x only data in its illumination window is used by a set illumination weight $w_i(x)$ to be a trapezoid. The illumination angular range for voxel x is defined by the sunrise angular position $\theta_f(x)$ and the sunset position $\theta_l(x)$. It is known that the illumination projections may be interrupted, thus the central continuous window is taken by ignoring the small isolated windows to simplify the process.

Typically the pitch is set to be less than 0.3. Such a small pitch implies a huge data set, thus if each voxel is reconstructed by checking all available projections the computation will be extremely slow and impractical to implement. Thus the illumination range is typically computed for each voxel first to exclude a large number of projections. However, the illumination range computation itself is not an easy task and can take a significant amount of time since the illumination range is different for every voxel.

Thus, according to the disclosure an efficient algorithm accelerates the illumination range computation. To better illustrate the disclosed subject matter, first a "brute force" set of steps illustrated in FIG. 6 is discussed, and an accelerated version according to the disclosure is illustrated in FIG. 7.

Figure 6:
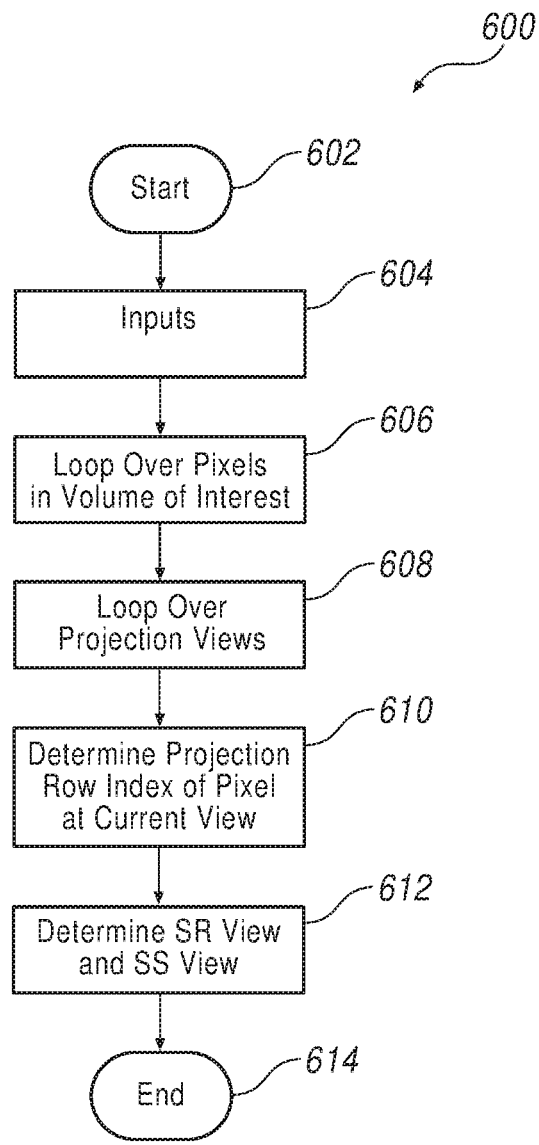
FIG. 6 illustrates steps for a known or 'brute force' computation to determine an illumination range for a retrospective helical cardiac reconstruction.
Figure 7:
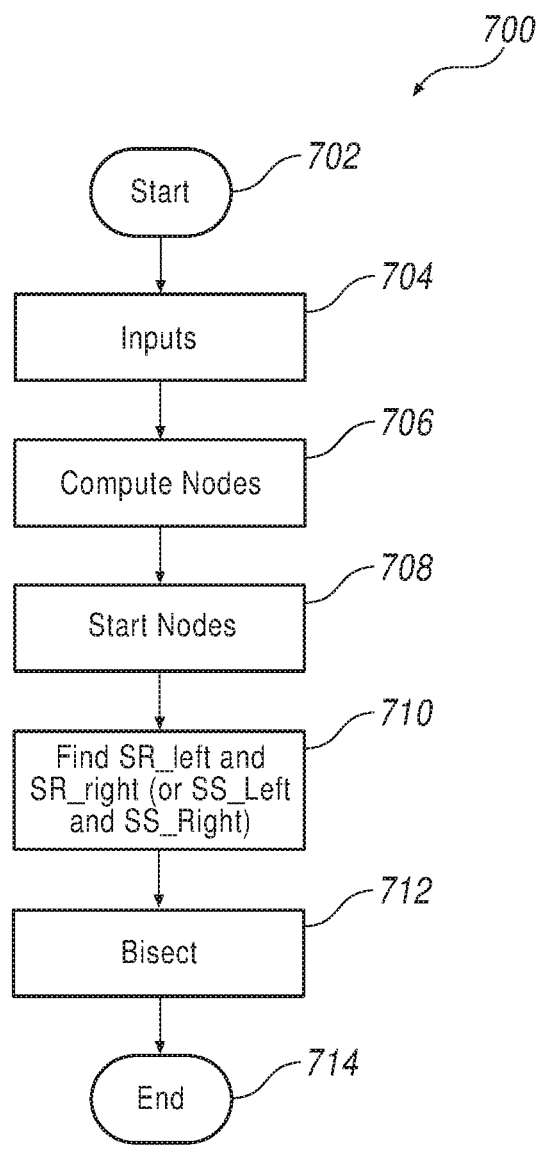
FIG. 7 illustrates steps for an accelerated determination of the illumination range, according to the disclosure.

Referring to FIG. 6, a regular or known "brute force" set of steps 600 for SR and SS computation are shown. Starting at step 602, at step 604 a set of inputs and assumptions include:

1. The global coordinate origin is the system isocenter (which, as is known, may not be not the image center).
2. Projection angles $\theta = \theta_0 + \Theta = \theta_0 + p\Delta\theta$, p=0, 1, 2, ..., M−1. Both $\Theta$ and $\theta$ are vectors with length M, and $\Delta\theta$ is the gantry moving step size.

3. The source has z-coordinate $z_0$ for the initial native projection at angular position $\beta_0$.

4. The detector row index increases direction is the same as z-axis positive direction.

Referring still to FIG. 6, the following steps and equations are referred to. That is, the illumination range is computed as follows. For a given voxel $I(x, y, z_k)$, the SR and SS view positions are determined as $S(x, y, k)$ and $E(x, y, k)$, respectively.

1. Determine $\Theta_p = p \cdot \Delta\theta$, $p=0, 1, 2, \ldots, M-1$.
2. Convert 2D coordinates (x, y) to polar coordinates:

$$\phi = \phi(x, y), \rho = \sqrt{x^2 + y^2} ; \qquad \text{Eqn. 2.}$$

3. Determine:

$$t = x \cdot \cos(\theta) + y \cdot \sin(\theta); \qquad \text{Eqn. 3.}$$

4. Determine:

$$L = \sqrt{D^2 - t^2} + x \cdot \sin(\theta) - y \cdot \cos(\theta); \qquad \text{Eqn. 4.}$$

Here, D is the source to system isocenter distance.

5. For all p compute:
Here, $$B_p = \Theta_p - \gamma; \qquad \text{Eqn. 5.}$$

$$\gamma = \arcsin\left(\frac{t}{D}\right).$$

6. For all p compute:

$$z_p = z_0 + \frac{-\chi \beta_p H \cdot h}{2\pi} = z_0 + \frac{-\chi(\Theta_p - \gamma) H \cdot h}{2\pi} ; \qquad \text{Eqn. 6.}$$

Here, h represents the pitch, H the full detector height and $\chi(=+1$ or $-1)$ the table moving direction, and $\Theta$ denotes the angle change.

7. For all p compute $$q = \frac{D * (z_k - z_p)}{L} ; \qquad \text{Eqn. 7.}$$

8. Let $p_s$ be the index of the last elements, start from 0, in q such that:

$$\chi \cdot q > H/2; \qquad \text{Eqn. 8.}$$

and $p_s$ be the index of the first elements in q such that:

$$\chi \cdot q < -H/2; \qquad \text{Eqn. 9.}$$

then:

$$S(x,y,k) = p_s + 1; \qquad \text{Eqn. 10, and}$$

$$E(x,y,k) = p_e - 1 \qquad \text{Eqn. 11.}$$

Referring back to FIG. 6, still referring to step 604, inputs include step 1 shown above, pixel positions of $(x, y, z_k)$, source to isocenter distance D, pitch h, detector height H, and table movement direction $\kappa(=+1$ or $-1)$. At step 606 the pixels are looped over in the volume of interest, and at step 608 the projection views are looped over. At step 610 the projection row index of the pixel at the current view is determined using Eqn. 7, and stepping through Eqns. 2 through 6.

At step 612 and for the current pixel $(x, y, z_k)$, the SR view is the view immediately after the last view which satisfies Eqn. 8, and the SS view is the view. immediately before the first view that satisfies Eqn. 9.

Thus, according to the disclosure, to accelerate the illumination range computation, S (Eqn. 10) and E (Eqn. 11) are determined for a single image slice, e.g. slice k: $I(x, y, z_k)$, and shift the numbers for other slices.

For example, let k* be the slice crossing the middle of the scan projections view p*=floor(M/2). S(x,y,k*) and E(x,y,k*) have already been computed, so for all other slices, the index images S(x,y,k*) and E(x,y,k*) only need be rotated with angle (p–p*) $\Delta\theta$, where p is the projection index at which the target image slice k crosses the source trajectory.

Following notations are introduced:

$$a = \frac{Hh}{2\pi}, v = \frac{H}{2D}, b = -v\rho, \overline{b} = -b; \qquad \text{Eqn. 12.}$$

Functions $f(\Theta)$ and $g(\Theta)$ are introduced as well:

$$f(\Theta) = a\Theta - v(x \cdot \sin(\Theta) - y \cdot \cos(\Theta) - a \cdot \gamma(\Theta) + \sqrt{D^2 - t^2(\Theta)}) + x(z_k - z_0); \qquad \text{Eqn. 13.}$$

$$g(\Theta) = a\Theta + v(x \cdot \sin(\Theta) - y \cdot \cos(\Theta) - a \cdot \gamma(\Theta) + \sqrt{D^2 - t^2(\Theta)}) + x(z_k - z_0); \qquad \text{Eqn. 14.}$$

Inequalities of Equations 8 and 9 are rewritten to:

$$f(\Theta) > 0, g(\Theta) < 0. \qquad \text{Eqn. 15.}$$

First and second order derivatives of $f(\Theta)$ and $g(\Theta)$ can be determined analytically.

And, according to the disclosure, a fast algorithm to compute $p_s$ and $p_e$, as shown in FIG. 7. As such, details of fast computation of the illumination range, i.e. the sunrise (SR) and sunset (SS) of each voxel are disclosed.

Starting at step 702, let id0 be the index such that $\theta(\text{id0}) \approx \theta_0$, let m be the index of the element in vector $\Theta$ such that the image slice k intersects the source trajectory. Calculate the start and end illumination view index, $p_s$ and $p_e$, of one pixel in image slice $z = z_k$.

At step 704, inputs include step 1 shown above, pixel positions of $(x, y, z_k)$, source to isocenter distance D, pitch h, detector height H, and table movement direction $\kappa(=+1$ or $-1)$ At step 706 the nodes are determined by applying steps in FIG. 8 (discussed below) to compute the "nodes", SRnodes and SSnodes, i.e. the stable points of functions $f(\Theta)$ and $g(\Theta)$.

At step 708 the SRnodes are sorted in descending order and SSnodes are sorted in ascending order.

At step 710 SR_left and SR_right are found such that:

$$f(\Theta)[\text{SR\_left}] > 0; \qquad \text{Eqn. 16; and}$$

$$f(\Theta)[\text{SR\_right}] < 0; \qquad \text{Eqn. 17.}$$

Loop over SRnodes to find the last index k such that $f(\Theta)[SRnodes(k)])>0$, then set:

SR_left=SRnodes(k) or 1 if no such k;

SR_right=SRnodes(k+1) or m when k==1.

At step 710 SS_left and SS_right are determined in the same fashion.

At step 712 a bisection step is applied to determine $p_s$ and $p_e$:

$p_s$=bisect(SR_left, SR_right, f);      Eqn. 18; and $p_e$=bisect(SS_left, SS_right, g).      Eqn. 19.

Figure 8:
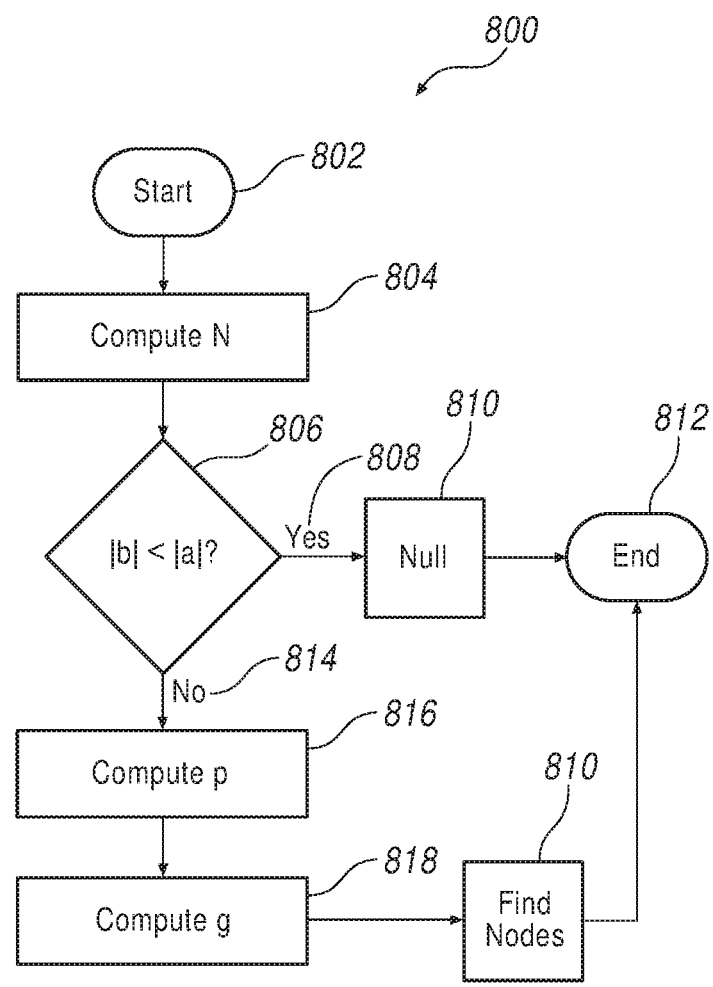
FIG. 8 illustrates steps for determining nodes, according to the disclosure, as a subset of steps for use in FIG. 7.

Referring now FIG. 8, steps 800 pertaining to step 706 above and as described in FIG. 7 follow.

Starting at step 802, at step 804 N is determined: N=round $(2\pi/\Delta\theta)$.

At step 806, if |b|<|a|, 808, then null or empty sets are returned and SRnodes=SSnode={ } and the process ends at step 812. If not, 814, then p is determined at step 816:

$$p = \text{round}\left(\frac{\cos^{-1}(-a/b)+\phi}{\Delta\theta}\right); \quad \text{Eqn. 20.}$$

At step 818 q is determined:

q=p+N/2;      Eqn. 21.

Thus, p and q are estimates of representative nodes of the two categories.

As necessary, p and q may be refined using, for instance, a Newton method. Typically one step may be sufficient.

At step 820 the nodes are determined:

$$K = \left\{k : |p+kN| \leq \frac{N(D+FOV/2)}{2D*h} \text{ and } |q+kN| \leq \frac{N(D+FOV/2)}{2D*h}\right\}; \quad \text{Eqn. 22;}$$

and

SRnodes={id0+p+kN: id0+p+kN>0 and id0+p+kN<m} $\cup$ {id0+q+kN>0 and id0+q+kN<m};      Eqn. 23.

Similarly, sunset notes SSnodes may be determined, as well.

Thus, the set SRnodes is built by checking a small number of integers within set K at Eqn. 24 such that the condition at Eqn. 25 is satisfied.

Thus, according to the disclosure, a computed tomography (CT) system includes a rotatable gantry having an opening to receive an object to be scanned, an x-ray tube, a pixelated detector positioned on the rotatable gantry to receive the x-rays from the x-ray tube, and a computer programmed to acquire helical CT data, determine a sunrise (SR) view position for each pixel within a SR index image, and determine a sunset (SS) view position for each pixel within a SS index image, for a given reference image slice, wherein the SR view position is a first angle of an illumination range for a voxel and the SS view position is a last angle of the illumination range for the voxel, for all slices, rotate the SR index image and the SS index image through a projection index, and reconstruct an image based on the rotated SR index image and the SS index image.

Also according to the disclosure, a method of computed tomography (CT) imaging includes rotating an object on a rotatable CT gantry, generating x-rays toward the object from an x-ray tube, positioning a pixelated detector on the rotatable gantry to receive the x-rays from the x-ray tube, acquiring helical CT data, determining a sunrise (SR) view position for each pixel within a SR index image, and a sunset (SS) view position for each pixel within a SS index image, for a given reference image slice, wherein the SR view position is a first angle of an illumination range for a voxel and the SS view position is a last angle of the illumination range for the voxel, for all slices, mathematically rotating the SR index image and the SS index image through a projection index, and reconstructing an image based on the rotated SR index image and the SS index image.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A computed tomography (CT) system, comprising:
   a rotatable gantry having an opening to receive an object to be scanned;
   an x-ray tube;
   a pixelated detector positioned on the rotatable gantry to receive the x-rays from the x-ray tube; and
   a computer programmed to:
      acquire helical CT data;
      determine a sunrise (SR) view position for each pixel within a SR index image, and determine a sunset (SS) view position for each pixel within a SS index image, for a given reference image slice, wherein the SR view position is a first angle of an illumination range for a voxel and the SS view position is a last angle of the illumination range for the voxel;
      for all slices, rotate the SR index image and the SS index image through a projection index; and
      reconstruct an image based on the rotated SR index image and the SS index image.

2. The CT system of claim 1, wherein the computer is programmed to determine the SR index image and the SS index image at a slice crossing a middle of a scan projection.

3. The CT system of claim 1, wherein the computer is programmed to determine the projection index at which a target image slice crosses a source trajectory.

4. The CT system of claim 1, wherein the computer is programmed to determine the projection index as a first projection index corresponding to the SR index image and as a second projection index corresponding to the SS index image.

5. The CT system of claim 4, wherein the computer is programmed to determine the first and second projection indexes by defining functions that correspond with the SR and SS positions.

6. The CT system of claim 5, wherein the computer is programmed to determine nodes corresponding to mathematically stable points of the functions.

7. A method of computed tomography (CT) imaging, comprising:
   rotating an object on a rotatable CT gantry;
   generating x-rays toward the object from an x-ray tube;
   positioning a pixelated detector on the rotatable gantry to receive the x-rays from the x-ray tube;
   acquiring helical CT data;
   determining a sunrise (SR) view position for each pixel within a SR index image, and a sunset (SS) view position for each pixel within a SS index image, for a given reference image slice, wherein the SR view position is a first angle of an illumination range for a voxel and the SS view position is a last angle of the illumination range for the voxel;
   for all slices, mathematically rotating the SR index image and the SS index image through a projection index; and
   reconstructing an image based on the rotated SR index image and the SS index image.

8. The method of claim 7, further comprising determining the SR index image and the SS index image at a slice crossing a middle of a scan projection.

9. The method of claim 7, further comprising determining the projection index at which a target image slice crosses a source trajectory.

10. The method of claim 7, further comprising determining the projection index as a first projection index corresponding to the SR index image and as a second projection index corresponding to the SS index image.

11. The method of claim 10, further comprising determining the first and second projection indexes by defining functions that correspond with the SR and SS positions.

12. The method of claim 11, further comprising determining nodes corresponding to mathematically stable points of the functions.

13. A non-transitory computer-readable medium tangibly embodying computer-executable instructions of a program being executable by a hardware processor of a computing device with a user interface to provide operations comprising:
   rotating an object on a rotatable CT gantry;
   generating x-rays toward the object from an x-ray tube;
   positioning a pixelated detector on the rotatable gantry to receive the x-rays from the x-ray tube;
   acquiring helical CT data;
   determining a sunrise (SR) view position for each pixel within a SR index image, and a sunset (SS) view position for each pixel within a SS index image, for a given reference image slice, wherein the SR view position is a first angle of an illumination range for a voxel and the SS view position is a last angle of the illumination range for the voxel;
   for all slices, mathematically rotating the SR index image and the SS index image through a projection index; and
   reconstructing an image based on the rotated SR index image and the SS index image.

14. The medium of claim 13, the operations further comprising determining the SR index image and the SS index image at a slice crossing a middle of a scan projection.

15. The medium of claim 13, the operations further comprising determining the projection index at which a target image slice crosses a source trajectory.

16. The medium of claim 13, the operations further comprising determining the projection index as a first projection index corresponding to the SR index image and as a second projection index corresponding to the SS index image.

17. The medium of claim 16, the operations further comprising determining the first and second projection indexes by defining functions that correspond with the SR and SS positions.

18. The medium of claim 17, the operations further comprising determining nodes corresponding to mathematically stable points of the functions.

* * * * *